United States Patent [19]

Montillier

[11] 3,975,196

[45] Aug. 17, 1976

[54] PHOTOCONDUCTIVE CHARGE TRANSFER COMPLEX FOR ELECTROPHOTOGRAPHY

[75] Inventor: Jean-Pierre Montillier, Manchester, Conn.

[73] Assignee: Pitney-Bowes, Inc., Stamford, Conn.

[22] Filed: Mar. 20, 1972

[21] Appl. No.: 236,196

[52] U.S. Cl. .................................. 96/1.5; 260/315
[51] Int. Cl.$^2$ ........................................ G03G 5/06
[58] Field of Search ...................... 96/1.5; 252/501; 260/315

[56] References Cited
UNITED STATES PATENTS

| | | | |
|---|---|---|---|
| 3,113,022 | 12/1963 | Cassiers et al. ..................... | 96/1.5 X |
| 3,287,120 | 11/1966 | Hoegl .................................. | 96/1.5 |
| 3,484,237 | 12/1969 | Shattuck et al. .................... | 96/1.5 |
| 3,542,546 | 11/1970 | Fox ..................................... | 96/1.5 |
| 3,655,378 | 4/1972 | Contois et al. ...................... | 96/1.5 |
| 3,661,879 | 5/1972 | Van Dam et al. ................... | 96/1.5 X |
| 3,666,458 | 5/1972 | Arneth et al. ....................... | 96/1.5 X |
| 3,684,506 | 8/1972 | Guarnaccio ......................... | 96/1.5 X |
| 3,811,879 | 5/1974 | Montillier ........................... | 96/1.5 C |

*Primary Examiner*—David Klein
*Assistant Examiner*—John R. Miller
*Attorney, Agent, or Firm*—Peter Vrahotes; William D. Soltow, Jr.; Albert W. Scribner

[57] ABSTRACT

Photoconductive materials are prepared from a dicarbazolyl compound and a Lewis acid. The materials are charge transfer complexes, with the dicarbazolyl compound, such as 1, 2-dicarbazolyl cyclobutane acting as an electron donor and the Lewis acid, such as 2, 4, 7-trinitro-9-fluorenone acting as an electron acceptor. The molar ratio of the donor to the acceptor can be in the range from 1:0.5 to 1:5.

3 Claims, No Drawings

PHOTOCONDUCTIVE CHARGE TRANSFER COMPLEX FOR ELECTROPHOTOGRAPHY

BACKGROUND OF THE INVENTION

1. Field of the Invention

This invention relates to an organic photoconductive composition comprising dicarbazolyl cyclobutane, and more particularly, to the use of dicarbazolyl cyclobutane in combination with a nitrofluorenone and their use in electrophotographic processes.

2. Description of the Prior Art

The forming and developing of images on the surfaces of certain photoconductive materials, by electrostatic means, is now well known. Carlson, in U.S. Pat. No. 2,297,691 teaches the basic xerographic process, which involves uniformly charging a photoconductive insulating layer and then exposing the layer to a light-and-shadow image which dissipates the charge on the portions of the layer which are exposed to light. The electrostatic latent image formed on the layer corresponds to the configuration of the light-and-shadow image. In another modification, a latent electrostatic image is formed on the photoconductive insulating layer by charging the layer in image configuration. A finely divided developing material comprising a colorant called a toner and a toner carrier is deposited on the image layer. The developing material is normally attracted to those portions of the layer which retain a charge, thereby forming a powder image corresponding to the latent electrostatic image. The powder image may then be transferred to paper or any other receiving surface. The powder image is permanently bonded to the paper by any suitable fixing means. Typically, a heating process, called fusing, is used, as described in U.S. Patents such as, U.S. Pat. Nos. 2,357,809; 2,891,011 and 3,079,342.

It is possible to employ a wide variety of photoconductive insulating materials in the electrostatic process. For example, Carlson, in U.S. Pat. No. 2,297,691 discloses photoconductive insulating materials such as anthracene, sulfur, selenium or mixtures thereof.

These materials generally have sensitivity in the blue or near ultraviolet range, and all but selenium have a further limitation of being only slightly light sensitive. For this reason, selenium has been the most commercially accepted material for use in electrophotographic plates. Vitreous selenium, however, while desirable in most aspects, suffers from serious limitations in that its spectral response is somewhat limited to the ultra-violet, blue and green region of the spectrum, and the preparation of vitreous selenium plates requires costly and complex procedures, such as vacuum evaporation. Also, selenium plates require the use of a separate conductive substrate layer, preferably with an additional barrier layer deposited thereon before deposition of the selenium photoconductor. Because of these economic and commercial considerations, there have been many recent efforts towards developing photoconductive insulating materials other than selenium for use in electrophotographic plates.

It has been proposed that various two-component materials be used in photoconductive insulating layers used in electrophotographic plates. For example, the use of inorganic photoconductive pigment dispersed in suitable binder materials to form photoconductive insulating layers is known. It has further been demonstrated that organic photoconductive insulating dyes and a wide variety of polycyclic compounds may be used together with suitable resin materials to form photoconductive insulating layers useful in binder-type plates. In each of these two systems, it is necessary that at least one original component used to prepare the photoconductive insulating layer be, itself, a photoconductive insulating material.

In a third type plate, inherently photoconductive polymers are used; frequently in combination with sensitizing dyes or Lewis acids to form photoconductive insulating layers. Again, in these plates at least one photoconductive insulating component is necessary in the formation of the layer. While the concept of sensitizing photoconductors is itself commercially useful, it does have the drawback of being limited to only those materials already having substantial photoconductivity.

The above discussed three types of known plates are further described in U.S. Pat. Nos. 3,097,095; 3,113,022; 3,041,165; 3,126,281; 3,073,861; 3,072,479; 2,999,750; Canadian Pat. No. 644,167 and German Pat. No. 1,068,115.

The polymeric and binder-type organic photoconductor plates of the prior art generally have the inherent disadvantages of high cost of manufacture, brittleness, and poor adhesion to supporting substrates. A number of these photoconductive insulating layers have low temperature distortion properties which make them undesirable in an automatic electrophotographic apparatus which often includes powerful lamps and thermal fusing devices which tend to heat the xerographic plate. Also, the choice of physical properties has been limited by the necessity of using only inherently photoconductive materials.

Inorganic pigment-binder plates are limited in usefulness because they are often opaque and are thus limited to use in systems where light transmission is not required. Inorganic pigment-binder plates have the further disadvantage of being nonreusable due to high fatigue and rough surfaces which make cleaning difficult. Still another disadvantage is that the materials used have been limited to those having inherent photoconductive insulating properties.

The use of poly-N-vinylcarbazole alone, or in combination with trinitro-fluorenone, as a photoconductor is taught in the prior art, as for example, in U.S. Pat. No. 3,037,861 to Hoegl and U.S. Pat. No. 3,484,237 to Shattuck et al.

The preparation of coatings of poly-N-vinyl carbazole and trinitro-fluorenone involves dissolving the polymerized vinylcarbazole in a solvent such as tetrahydrofuran, benzene, toluene, dioxane or dichloro methane followed by the addition of 2, 4, 7-trinitro-9-fluorenone to the polymer solution and mixing the solution for about 30 minutes to more than an hour. The difficulty of dissolving the polymer tends to increase processing time and increase the complexity of the process.

The N-vinyl-carbazole monomer is very soluble in organic solvents but is a very poor photoconductor. The monomer forms an orange charge transfer complex with trinitro-fluorenone which is very insoluble even in tetrahydrofuran and is a very poor photoconductor.

SUMMARY OF THE INVENTION

It is an object of the invention to provide a composition which is photoconductive and can readily be processed so as to form a photoconductive structure.

It is another object of this invention to provide a photoconductive insulating material devoid of the above noted disadvantages.

It has now been found that the problems of the prior art can be overcome through the use of a Lewis acid, preferably trinitro-fluorenone in combination with a dicarbazolyl compound characterized by the following formula:

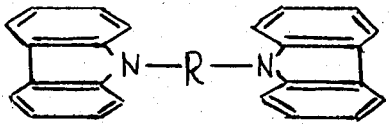

wherein R is a member selected from the group consisting of aryls alkyls and cycloalkyls. Preferably the dicarbazolyl compound is 1, 2-dicarbazolyl cyclobutane.

DESCRIPTION OF THE PREFERRED EMBODIMENT

The photoconductive material adaptable for use in electrophotographic processes includes an electron donor and an electron acceptor in the form of a charge transfer complex. While the mechanism of the complex chemical interreaction involved in the present process is not completely understood, it is believed that a "charge transfer complex" is formed having absorption bands characteristic of neither of the two components considered individually. The mixture of the two non or poorly photoconductive components seems to have a synergistic effect which is much greater than additive.

The electron donor is preferably a dicarbazolyl cycloalkane, but the cycloalkyl group can also be replaced by an alkyl or aryl group. The mole ratio of the dicarbazolyl compound to the Lewis acid can be in the range from 1:0.5 to 1:5, but is preferably from 1:1.5 to 1:3.5.

The electron acceptor can be a suitable Lewis acid and best results are obtained when using these preferred Lewis acids: 2, 4, 7-trinitro-9-fluorenone and 2, 4, 5, 7-tetranitro-9-fluorenone.

Other typical Lewis acids are: quinones, such as p-benzoquinone, 2, 5-dichlorobenzoquinone, 2, 6-dichlorobenzoquinone, chloranil, naphthoquinone-(1, 4), 2, 3-dichloronaphthoquinone-(1, 4), anthraquinone, 2-methylanthraquinone, 1, 4-dimethylanthraquinone, 1-chloroanthraquinone, anthraquinone-2-carboxylic acid, 1, 5-dichloroanthraquinone, 1-chloro-4-nitroanthraquinone, phenanthrenequinone, acenaphthenequinone, pyranthrenequinone, chrysenequinone, thio-naphthene-quinone, anthraquinone-1, 8-disulfonic acid and anthraquinone-2-aldehyde; triphthaloylbenzene-aldehydes such as bromal, 4-nitrobenzaldehyde, 2, 6-dichlorobenzaldehyde-2, ethoxyl-1-naphthaldehyde, anthracene-9-aldehyde, pyrene-3-aldehyde, oxindole-3-aldehyde, pyridine-2, 6-dialdehyde, biphenyl-4-aldehyde; organic phosphonic acid such as 4-chloro-3-nitrobenzene-phosphonic acid, nitrophenols, such as 4-nitrophenol, and picric acid; acid anhydrides, for example, acetic-anhydride, succinic anhydride, maleic anhydride, phthalic anhydride, tetrachlorophthalic anhydride, perylene-3, 4, 9, 10-tetracarboxylic acid and chrysene-2, 3, 8, 9-tetracarboxylic anhydride, dibromo maleic acid anhydride, metal halides of the metals and metalloids of the groups IB, II through to group VIII of the periodical system, for example: aluminum chloride, zinc chloride, ferric chloride, tin tetrachloride, (stannic chloride), arsenic trichloride, stannous chloride, antimony pentachloride, magesium chloride, magnesium bromide, calcium bromide, calcium iodide, strontium bromide, chromic bromide, manganous chloride, colbaltous chloride, cobaltic chloride, cupric bromide, ceric chloride, thorium chloride, arsenic tri-iodide; boron halide compounds, for example: boron trifluoride, and boron trichloride; and ketones, such as acetophenone, benzophenone, 2-acetylnaphthalene, benzil, benzoin, 5-benzoyl acenaphthene, biacene-dione, 9-acetyl-anthracene, 9-benzoyl-anthracene, 4-(4-dimethyl-amino-cinnamoyl)-1-acetylbenzene, acetoacetic acid anilide, indandione-(1, 3), (1-3-diketo-hydrindene,) acenaphthene quinonedichloride, anisil, 2, 2-pyridil and furil.

Additional Lewis acids are mineral acids such as the hydrogen halides, sulphuric acid and phosphoric acid; organic carboxylic acids, such as acetic acid and the substitution products thereof, monochloro-acetic acid, dichloroacetic acid, trichloro-acetic acid, phenylacetic acid, and 6-methylcoumarinylacetic acid (4); maleic acid, cinnamic acid, benzoic acid, 1-(4-diethyl-amino-benzoyl)-benzene-2-carboxylic acid, phthalic acid, and tetra-chlorophthalic acid, alph-beta-dibromo-beta-formyl-acrylic acid (mucobromic acid), dibromo-maleic acid, 2-bromo-benzoic acid, gallic acid, 3-nitro-2-hydroxyl-1-benzoic acid, 2-nitro phenoxy-acetic acid, 2-nitro-benzoic acid, 4-nitro-benzoic acid, 3-nitro-4-ethoxy-benzoic acid, 2-chloro-4-nitro-1-benzoic acid, 3-nitro-4-methoxy-benzoic acid, 4-nitro-1-methyl-benzoic acid, 2-chloro-5-nitro-1-benzoic acid, 3-chloro-6-nitro-1-benzoic acid, 4-chloro-3-nitro-1-benzoic acid, 5-chloro-3-nitro-2-hydroxybenzoic acid, 4-chloro-2-hydroxy-benzoic acid, 2, 4-dinitro-1-benzoic acid, 2-bromo-5-nitro-benzoic acid, 4-chlorophenyl-acetic acid, 2-chloro-cinnamic acid, 2-cyano-cinnamic acid, 2, 4-dichlorobenzoic acid, 3, 5-dinitro-benzoic acid 3, 5-dinitro-salycylic acid, malonic acid, mucic acid, acetosalycylic acid, benzilic acid, butane-tetra-carboxylic acid, citric acid, cyano-acetic acid, cyclo-hexane-dicarboxylic acid, cyclo-hexane-carboxylic acid, 9, 10-dichloro-stearic acid, fumaric acid, itaconic acid, levulinic acid, (levulic acid,) malic acid, succinic acid, alpha-bromo-stearic acid, citraconic acid, dibromo-succinic acid, pyrene-2, 3, 7, 8-tetra-carboxylic acid, tartaric acid; organic sulphonic acids, such as 4-toluene sulphonic acid, and benzene sulphonic acid, 2, 4-dinitro-1-methyl-benzene-6-sulphonic acid, 2, 6-dinitro-1-hydroxy-benzene-4-sulphonic acid, 2-nitro-1-hydroxy-benzene-4-sulphonic acid, 4-nitro-hydroxy-2-benzene-sulphonic acid, 3-nitro-2-methyl-1-hydroxy-benzene-5-sulphonic acid, 6-nitro-4-methyl-1-hydroxy-benzene-2-sulphonic acid, 4-chloro-1-hydroxy-benzene-3-sulphonic acid, 2 - chloro - 3-nitro - 1 -methyl-benzene-5-sulphonic acid and 2 - chloro-1-methyl-benzene-4-sulphonic acid.

The preferred electron donor according to the invention is dicarbazolyl cyclobutane. Its use alone as a photoconductor is at best difficult as evidenced by a test in which dicarbazolyl cyclobutane was coated on an aluminum foil to a thickness of 0.2 mil and taped on an 8 inch diameter drum. Measurements were made using a Monroe electrometer, and as the light source a Varian Xenon H.P. 15 Watt lamp with a Kodak neutral density filter 1.0. In the conditions of the experiment, the sample was charged to 460 volts and then exposed to the 900 Foot candle light source. It took 5.1 seconds for the voltage to be reduced by half ($t$ ½ = 4600 Foot candle seconds). In the same conditions a 0.2 mil coating of mono-N-vinyl carbazole showed a charge acceptance of only 80 volts and required more than 10 seconds to reduce it by half, thus showing that it has almost no photoconductivity.

A 0.2 mil coating of poly-N-vinyl carbazole similarly tested had a charge acceptance of 460 volts and required only 2.2 seconds to reduce it by half. ($t$ ½ = 2000 Foot candle seconds)

By way of contrast a 0.35 mil coating of a 1:2 molecular complex of dicarbazolyl cyclobutane and trinitrofluorenone was charged to 800 volts, and using a 1 foot candle tungsten light source, required only 1.5 seconds to reduce the voltage by half ($t$ ½ = 1.5 Foot candle second). Another coating only 0.2 mil thick had a charge acceptance of 400 volts and required only 1.1 seconds to discharge to one half of its original value.

It is thus evident that the dicarbazolyl cyclobutane-trinitro-fluorenone complex has a sensitivity at least 1000 times higher than that of N-vinyl carbazole or poly-N-vinyl carbazole, which makes it comparable in speed to selenium.

Another essential feature of the present invention is that although dicarbazolyl cyclobutane and trinitrofluorenone are both crystalline and therefore, at best, difficult to form into effective coatings (if used alone), their complex is amorphous and forms stable coatings which do not crystallize even upon long oven curing, and with ratios of trinitro-fluorenone up to 5 moles for 1 mole of dicarbazolyl cyclobutane.

Another advantage of the composition of this invention is that because it is highly colored (dark brown), the sometimes complex use of sensitizing dyes can be avoided.

The dicarbazolyl cyclobutane can be produced by any convenient procedure, as for example disclosed by Wang, Sizman and Stevenson in the Journal of Organic Chemistry, Vol. 35, No. 6, pg. 2045 (1970) and by Shirota et al., in Chemical Communications, pg. 1110 (1970)

The following examples will further define the specifics of the present invention. Parts and percentages are by weight unless otherwise indicated. The examples below should be considered to illustrate various preferred embodiments of the present invention:

EXAMPLE I

To a solution of 100 grams (0.518 mole) of N-vinyl carbazole (Borden Chemicals), melting point 67°C, in 1,500 milliliters (ml.) of absolute ethanol, was added 2 grams ($4.95 \times 10^{-3}$ mole) of ferric nitrate (Mallinckrodt), $Fe(NO_3)_3 \cdot 9H_2O$ in 100 ml. of ethanol. The mixture was stirred at room temperature with strong bubbling of air in the solution; and a white precipitate gradually appeared. At the end of 2 hours a 95% pure solid was collected, and recrystallized from a mixture of acetone and ethanol in a 3 to 1 ratio. The yield was in the 30 to 40 gram range (30 to 40% of theoretical), had a melting point of 197°C and had the appearance of white needles.

The calculated analysis for $C_{28} H_{22} N_2$ is C, 87.04; H, 5,69; N, 7,25; mol weight, 386.5. The observed analysis was C, 86.93; H, 5.87; N, 7.22. NMR and IR analysis proved the material to be pure 1, 2 dicarbazolyl cyclobutane.

Ten grams of the dicarbazolyl cyclobutane were dissolved in 43 ml. of dichloromethane and mixed with 16.3 grams of trinitrofluorenone dissolved in 80 ml. of tetrahydrofuran.

solution soltution was dip coated on a 3 mil aluminized Mylar substrate to a thickness of about 0.2 to 0.3 mil. After coating, the sample was cured for 5 minutes in an oven at 60°C.

The sample was tested in a Victoreen apparatus and was found to have a charge acceptance of 800 volts and required 1.5 seconds to reduce the potential to one half of its original value using 1 foot candle light. Dark decay was negligeable. A sample was placed in a Xerox Model D xerographic processor and photocopies of acceptable quality were produced.

EXAMPLE II

Two grams ($5.18 \times 10^{-3}$ mole) of dicarbazolyl cyclobutane were dissolved in 10 ml. of tetrahydrofuran. It takes less than a few seconds for complete dissolution. This solution is then combined with a solution of 0.815 gm. ($2.58 \times 10^{-3}$ mole) of 2, 4,7-trinitro-9-fluorenone. A dark brown color is immediately generated. The solution is then coated with a doctor blade on a 3 mil alluminized Mylar giving a 0.25 mil thick coating. After 5 minutes curing in an oven at 140°F, the sample analyzed on a Victoreen apparatus had a charge acceptance of 850 volts and required 1.8 foot candle seconds to reduce the voltage by one half.

EXAMPLE III

The procedure of Example II was followed except that 3.26 gm. ($1.03 \times 10^{-2}$ mole) of 2, 4,7-trinitro-9-fluorenone was used. A coating 0.25 mil thick was prepared. It had a charge acceptance of 800 volts, and required only 1.5 foot candle seconds to reduce it by half. There was practically no dark decay.

EXAMPLES IV and V

The procedure of Example II was followed except that 4.89 gm. ($1.55 \times 10^{-2}$ mole) in one case and 6.52 gm. ($2.07 \times 10^{-2}$ mole) in the other, of 2, 4, 7-trinitro-9-fluorenone was used.

Coatings prepared from these solutions using either a dip type or doctor blade type coating technique were excellent and did not show any sign of crystallization even upon extensive curing. Coatings 0.25 mil thick had a charge acceptance of 850 volts and required from 1.5 to 1.7 foot candle seconds to reduce the voltage by half.

EXAMPLE VI

The procedure of Example II was followed except that a solution of 3.74 gm. ($1.03 \times 10^{-2}$ mole) of 2, 4, 5, 7-tetranitro-9-fluorenone in 18 ml. of tetrahydrofuran was used instead of 2, 4, 7-trinitro-9-fluorenone.

The solution had a tendency to crystallize. However, an amorphous 0.15 mil coating, after 5 minutes of curing at 140°F had a charge acceptance of 400 volts and required 1.7 foot candle seconds to reduce the voltage by one half.

What is claimed is:

1. A photoconductive material for electrophotography comprising a charge transfer complex of 1,2 dicarbazolyl cyclobutane and 2,4,7-trintro-9-fluorenone, said dicarbazolyl cyclobutane and said trinitro-fluorenone being in a mole ratio of from about 1:0.5 to about 1:5.

2. A photoconductive material of claim 1 wherein the mole ratio of the carbazolyl compound to the fluorenone compound is from about 1:1.5 to about 1:3.5.

3. A photoconductive material for electrophotography comprising a charge transfer complex of one mole of 1,2 dicarbazolyl cyclobutane and two moles of 2,4,7-trinitro-9-fluorenone.

\* \* \* \* \*

UNITED STATES PATENT OFFICE
CERTIFICATE OF CORRECTION

Patent No. 3,975,196  Dated August 17, 1976

Inventor(s) Jean Pierre Montillier

It is certified that error appears in the above-identified patent and that said Letters Patent are hereby corrected as shown below:

Column 5, line 67, please remove the first occurrence of "solution" and insert the word --The--.

Signed and Sealed this

Twenty-eighth Day of December 1976

[SEAL]

Attest:

RUTH C. MASON
Attesting Officer

C. MARSHALL DANN
Commissioner of Patents and Trademarks

UNITED STATES PATENT OFFICE
CERTIFICATE OF CORRECTION

Patent No. 3,975,196     Dated August 17, 1976

Inventor(s) Jean Pierre Montillier

It is certified that error appears in the above-identified patent and that said Letters Patent are hereby corrected as shown below:

Claim 2, Column 6, line 64, change "1:1:5 to about 1:3:5" to read --1:1.5 to about 1:3.5--.

Signed and Sealed this twenty-third Day of August 1977

[SEAL]

Attest:

RUTH C. MASON
*Attesting Officer*

C. MARSHALL DANN
*Commissioner of Patents and Trademarks*